(12) United States Patent
Nascimento et al.

(10) Patent No.: US 6,225,517 B1
(45) Date of Patent: May 1, 2001

(54) ALKYLATION CATALYST, METHOD FOR PREPARING SAME, AND USE THEREOF IN ALKYLATION METHODS

(75) Inventors: Pedro Nascimento, Le Havre; Georges Szabo; Alain Milan, both of Montivilliers, all of (FR)

(73) Assignee: Total Raffinage Distribution S.A., Puteaux (FR)

( * ) Notice: Subject to any disclaimer, the term of this patent is extended or adjusted under 35 U.S.C. 154(b) by 0 days.

(21) Appl. No.: 09/455,783

(22) Filed: Dec. 7, 1999

Related U.S. Application Data

(62) Division of application No. 09/114,169, filed on Jul. 13, 1998, now abandoned, which is a continuation of application No. PCT/FR97/00045, filed on Jan. 19, 1997.

(30) Foreign Application Priority Data

Jan. 11, 1996 (FR) .................................................. 96 00248

(51) Int. Cl.$^7$ ................................ C07C 2/56; C07C 2/58

(52) U.S. Cl. ............................................ 585/709; 585/721
(58) Field of Search ..................................... 585/709, 721; 502/224, 340, 341, 344, 346, 415, 306, 317, 328

(56) References Cited

U.S. PATENT DOCUMENTS

| | | | | |
|---|---|---|---|---|
| 4,066,716 | * | 1/1978 | Herbstman et al. .................. | 585/732 |
| 4,977,124 | * | 12/1990 | Smith ................................... | 502/174 |
| 5,849,977 | * | 12/1998 | Kocal et al. ......................... | 585/729 |

* cited by examiner

*Primary Examiner*—Mark L. Bell
*Assistant Examiner*—Patricia L. Hailey
(74) *Attorney, Agent, or Firm*—Sughrue, Mion, Zinn, Macpeak & Seas, PLLC

(57) ABSTRACT

An alkylation catalyst including a least one porous refractory metal oxide with at least one halogen on the surface thereof. The catalyst contains 0.005–1 wt % of at least one metal from groups IA and IIA of the periodic table of the elements and is particularly useful in an isobutane alkylation method using light olefins.

12 Claims, No Drawings

ALKYLATION CATALYST, METHOD FOR PREPARING SAME, AND USE THEREOF IN ALKYLATION METHODS

This is a divisional of application Ser. No. 09/114,169 filed Jul. 13, 1998, now abandoned, which is a continuation of application No. PCT/FR97/00045 filed Jan. 10, 1997, the disclosures of which are incorporated herein by reference.

This invention relates to a new alkylation catalyst, its preparation process, and its use in alkylation processes, notably in the alkylation of isobutene by light olefins. It is to this particular application of this catalyst that we will refer to more specifically, because of its economic importance, but this invention is, of course, not limited to this application.

It is known that isobutene alkylation by light olefins— that have between three and five atoms (referred to as $C_3$ to $C_5$)—yields an alkylate which possesses a high octane level and minimal amounts of unsaturated or aromatic compounds. This interesting property allows the use of the alkylate in important gasoline formulation, which is currently being researched by the petroleum industry.

This type of reaction can be achieved only with acid or very acid catalysts, and not without a reduction of peripheral reactions such as polymerization, which produce unsaturated hydrocarbons. Among these catalysts, we should mention sulfuric acid and fluoric acid types, which are, during the alkylation process, placed in contact as liquids with the isoparrafin-olefin mix to form an emulsion. However, such processes pose serious security, corrosion, and environmental problems. Since several national legal bodies are adopting stricter restrictions in this area, specialists have had to turn toward the development of catalysts prepared with a base of solid acids.

Among these solid-acid catalysts, we should mention those of Lewis and/or of Bronsted, which have been set on various inorganic platforms, as described in patents U.S. Pat. Nos. 3,975,299, 3,852,371, 3,979,476, and 4,613,723. We can also mention solid-acid catalysts based on aluminia chloride, described in the patents U.S. Pat. Nos. 3,240,840, 3,523,142, 4,066,716, 4,083,800, 4,066,716, 4,113,657, 4,138,444, and 2,999,074. We can see, however, that these catalysts have an insufficient activity, a minor alkylation selectivity, and that they do not really provide the stability generally required of catalysts. Furthermore, certain catalysts require operating temperatures that are lower than the ambient temperature, and this increases operating costs.

SUMMARY OF THE INVENTION

While the Applicant was performing research, it was discovered, by a surprising method, that adding metals from groups IA and IIA of the Periodic Table of Elements to the solid-acid alumina chloride-based catalyst increases performance.

These are the objectives of this invention:

to augment the selectivity and/or stability of this type of catalyst, while maintaining a sufficient activity level in the alkylation of isobutene by light olefins, and to be able to perform the alkylation of the isobutene in a wide range of temperatures, especially near ambient temperature, thus making operation easier.

To this effect, the invention first aims to be an alkylation catalyst containing a porous alumina support, which has at least one halogen on its surface, and which between 0.005 and 1% of its weight is made up of at least one metal from the IA or IIA group of the Periodic Table of Elements.

The alumina, as the support surface, will have a porous density between 5 and 400 $m^2/g$ as determined by the B.E.T. method. The halogen on the support surface may be chloride, and its weight amount should be between 2 and 10%, preferably between 3 and 8%. The weight amount of the group IA or IIA (Periodic Table of Elements) metals will be best between 0.05 and 0.5%.

The catalyst, according to the invention, may eventually contain a metal from group VIII of the Periodic Table of Elements, in order to facilitate its regeneration (platinum for example).

The catalyst described in the invention may be prepared according to the preceding instructions, by usual manufacturing methods well known to professionals in this field. One of the preparation methods may consist, first, of laying the metal (or metals) from group IA or IIA of the Periodic Table of Elements by impregnation of the alumina support into a water-based solution which contains the salt of at least one of these metals. This water-based solution may be nitrate, chloride, or sulfate-based, but since, as described later, the catalyst must undergo a chlorinating, the Applicant therefore prefers to use a water-chlorine solution and one of the metals mentioned above. Of these metals, the Applicant has successfully tested lithium, sodium, potassium, cesium, magnesium, and barium.

The impregnation phase in the water-based metal-salt solution is then followed by a drying of the solution in an evaporation centrifuge.

After these two steps, the catalyst is dried at 120° C. then calcined in an oven at 500° C.

The catalyst support may also be impregnated by the so called dry impregnation method, well known from a previous technique, or by any other means of impregnation.

The second step is to chloride the impregnated support, using, for example, nitrogen or hydrogen-maintained anhydrous chlorhydric acid, at temperatures equal to or greater than 650°, or by any other chlorination method.

A second element of the invention is thus the manufacturing process of this catalyst, outlined in the following steps:

pre-impregnation of a porous alumina support by at least one salt of a metal from groups IA and/or IIA of the Periodic Table of Elements, dry or in a water-based solution, drying of the impregnated support, calcination of the support, and finally, chlorinating of the support.

The prepared catalyst is now ready to be used in the alkylation process, especially for the alkylation of isobutenes by light olefins, notably by butenes.

The following uses of the catalyst constitute other parts of the invention.

In the case of the alkylation of isobutenes by light olefins, the process can be realized under the following conditions:

temperature: between −20° and 100° C., preferably between −5° and 35° C., pressure: sufficient to maintain the elements in a liquid form within the reactor, hourly spatial speed: expressed in p.p.h. (weight of olefins passing on the catalyst by weight unit of the catalyst and by hour), between 0.001 and 10 $h^{-1}$, preferably between 0.05 and 3 $h^{-1}$, molar ratio of isobutene to olefins: between 1 and 100.

The reactor within which the alkylation occurs may uses the catalyst as a solid bed, a mobile bed, a fluid bed, or even in suspension in the efficiently agitated liquid phase of the reagents.

The Applicant has successfully used a reactor which uses the catalyst as a solid bed, which is then filled with isobutene prior to the beginning of the alkylation process, that is to say before the injection of the isobutene-olefins mix into the reactor. Working with an excess of isobutene in relation to olefins (molar relation between 1 and 100) restricts secondary reactions.

The activity of the catalyst is measured by the conversion of olefins.

The conversion of the olefins is calculated according to this formula:

$$\text{Conversion} = \frac{\text{rate of olefin mass input} - \text{rate of olefin mass output}}{\text{rate of olefin mass input}}$$

Furthermore, we know that the alkylate obtained from the alkylation of isobutene by light olefins contain different elements, such as and in particular, hydrocarbons $C_5$ to $C_7$, heavier hydrocarbons $C_8$, among which trimethylpentane (TMP) and dimethylhexanes (DMH), and finally of hydrocarbons heavy in $C_{9+}$.

The selectivity of the catalyst for alkylation is measured by:
  the selectivity of the obtained alkylates, represented by the selectivity in $C_{9+}$ compounds.
  the composition of the resulting alkylate, represented by:
  the rate of $C_5$–$C_7$ in the $C_{5+}$;
  the rate of $C_6$ in the $C_{5+}$;
  the rate of $C_{9+}$ in the $C_{5+}$.
According to the following formulas:

$$C_{5+} \text{ selectivity} = \frac{\text{Rate of } C_{5+} \text{ mass input}}{\text{Rate of olefins mass input} - \text{Rate of olefin mass output}}$$

$$\text{Fraction of the } C_5\text{–}C_7 \text{ in the } C_{5+} = \frac{\text{Rate of } [C_5 + C_6 + C_7] \text{ mass input}}{\text{Rate of } C_{5+} \text{ mass input}}$$

$$\text{Fraction of the } C_8 \text{ in the } C_{5+} = \frac{\text{Rate of } C_8 \text{ mass input}}{\text{Rate of } C_{5+} \text{ mass input}}$$

$$\text{Fraction of the } C_9 \text{ in the } C_{5+} = \frac{\text{Rate of } [C_9 + C_{9+}] \text{ mass input}}{\text{Rate of } C_{5+} \text{ mass input}}$$

When the alkylation is properly performed, meaning that the catalyst performs, the selectivity of $C_{5+}$ is in the neighborhood of 204% while maintaining satisfactory olefin conversion. This value may be slightly lesser or greater if secondary reactions occurs, such as, for example, an oligomization of olefins or an auto-alkylation of the isobutene.

Furthermore, as the following examples show, the catalyst in this invention yields an alkylate which contains a large quantity of $C_8$ and of TMP compounds, whose ratio in the $C_8$ is measured according to the following formula:

$$\frac{\text{Tmp}}{C_8} = \frac{\text{Rate of (2,2,4-tmp + 2,2,3-tmp + 2,3,4-tmp + 2,3,3-tmp) mass}}{\text{Rate of } C_8 \text{ mass}}$$

(The TMP compounds are a mix of the following isomers:

2,2,4-Trimethylpentane, 2,2,3-Trimethylpentane
2,3,4-Trimethylpentane, 2,3,3-Trimethylpentane).

DETAILED DESCRIPTION OF THE PREFERRED EMBODIMENTS

The following examples illustrate the invention's applications and displays its advantages, without limiting its scope.

EXAMPLE ONE

This example describes the preparation of a catalyst according to the previous method.

This catalyst, named A, is prepared by the following method.

The metallic refractory support of the catalyst is 25 grams of alumina, which has a BET-specific surface equal to 200 $m^2/g$.

This alumina is made available commercially by the AKZO company under the name of CK 300.

The catalyst is left overnight in nitrogen at 500° C. Then, it is submitted to a chlorinating by a gaseous mix of chlorhydric acid and hydrogen (ratio 80/20) at 670° C. for 2 hours.

The catalyst is therefore an alumina chloride containing about 5.5% of its mass as chloride.

EXAMPLE TWO

This example demonstrates the preparation of catalysts according to the invention.

The catalysts, referred to from B to G, are prepared according to the following instructions:

The refractory metallic support of the catalysts is the alumina used in example one. 50 grams of these supports are then impregnated by contact with a water-based solution of chloride of one of the metals from this group: lithium; sodium, potassium, cesium, magnesium, or barium.

The catalysts B, C, D, E, F, and G are respectively prepared from lithium, sodium, potassium, cesium, magnesium, and barium. Different concentration levels of these metals have been studied.

The water-based solution is then evaporated in a evaporation centrifuge and the catalysts thus obtained are dried at 120° C. then calcined at 500° C. for 2 hours in the oven.

The chlorinating of the catalysts is performed in the way described in example one.

For each catalyst thus prepared, the support contains between 5 and 6% in chloride weight and variable metal quantities, as Table 1 shows in Example Three.

EXAMPLE THREE

This example aims to compare the differences between catalyst A from the previous method and catalysts B–G of this invention's method, prepared in Examples One and Two.

These two types of catalysts are tested in the alkylation of isobutene by butenes reaction in the following conditions:

Charge: isobutene+butene-2-trans, with a molar ratio of isobutene to butene-2-trans around 14.

Mass of each catalyst: 8 grams

Temperature of reaction: 0° C.

Hourly spatial speed: expressed in p.p.h. (weight of olefins passing on the catalyst by weight unit of the catalyst and by hour), 0.25 $h^{-1}$.

Total reactor pressure: $30 \cdot 10^5$.

Before the beginning of the alkylation, the reactor is filled with nitrogen to the reaction pressure level, prior to the injection of the isobutene-butene-2-trans mix.

After the alkylation, calculate (for each of the catalysts A through G) the rate of conversion of the butenes, the selectivity of $C_{5+}$ compounds obtained, the ratio of $C_5$–$C_7$, $C_8$, $C_{9+}$ compounds obtained in the alkylate, as well as the ratio of TMP (trimethylpentane) compounds obtained in $C_8$ compounds, according to the following formulas.

$$\text{Conversion} = \frac{\text{rate of butene mass input} - \text{rate of butene mass output}}{\text{rate of butene mass input}}$$

$$C_{5+} \text{ selectivity} = \frac{\text{Rate of } C_5 \text{ mass input}}{\text{Rate of olefins mass input} - \text{Rate of olefin mass output}}$$

$$\text{Fraction of the } C_5\text{–}C_7 \text{ in the } C_{5+} = \frac{\text{Rate of } [C_5 + C_6 + C_7] \text{ mass input}}{\text{Rate of } C_{5+} \text{ mass input}}$$

$$\text{Fraction of the } C_8 \text{ in the } C_{5+} = \frac{\text{Rate of } C_8 \text{ mass input}}{\text{Rate of } C_{5+} \text{ mass input}}$$

$$\text{Fraction of the } C_{9+} \text{ in the } C_{5+} = \frac{\text{Rate of } [C_9 + C_{9+}] \text{ mass input}}{\text{Rate of } C_{5+} \text{ mass input}}$$

$$\frac{\text{tmp}}{C_8} = \frac{\text{Rate of } (2,2,4\text{-tmp} + 2,2,3\text{-tmp} + 2,3,4\text{-tmp} + 2,3,3\text{-tmp}) \text{ mass}}{\text{Rate of } C_8 \text{ mass}}$$

The following table shows these results:

TABLE 1

| Catalysts | A Nothing | B % In Weight of LI | | C % In Weight of Na | | D % In Weight of K | | E % In Weight of CS | | F % In Weight of Mg | G % In Weight of Ba |
|---|---|---|---|---|---|---|---|---|---|---|---|
| 5 Minutes of Use | Added | 0.05 | 0.25 | 0.50 | 0.05 | 0.25 | 0.20 | 0.40 | 0.20 | 0.40 | 0.60 | 0.5 |
| Conversion (%) | 93.4 | 96.0 | 98.6 | 89.4 | 91.9 | 95.2 | 87.0 | 77.3 | 86.8 | 84.6 | 83.88 | 90.4 |
| Selectivity $C_{5+}$ (%) | 238 | 231 | 226 | 212 | 256 | 212 | 216 | 203 | 243 | 229 | 186 | 237 |
| Alkylate Composition (%) | | | | | | | | | | | | |
| $C_5$–$C_7$ | 50.6 | 47.3 | 19.3 | 9.2 | 46.8 | 30.7 | 30.4 | 20.4 | 45.0 | 35.9 | 18.6 | 42.5 |
| $C_8$ | 39.8 | 43.1 | 74.8 | 85.7 | 43.5 | 60.9 | 60.3 | 70.7 | 43.1 | 53.4 | 74.2 | 46.9 |
| $C_{9+}$ | 9.6 | 9.5 | 5.9 | 5.1 | 9.8 | 8.2 | 9.3 | 8.8 | 11.8 | 10.8 | 7.1 | 10.7 |
| TMP/$C_8$ (%) | 69 | 73 | 94 | 97 | 74 | 86 | 84 | 90 | 71 | 77 | 91 | 75 |

These results show that the invention's catalysts B and G show a better quality alkylation, since the heavy $C_8$ compounds and especially TMP compounds are produced in greater quantity, while the conversion of butenes remains satisfactory.

EXAMPLE FOUR

This example aims to compare the performances of catalyst B according to the invention and of catalyst A according to the previously used method.

The alkylation reaction is performed in the same conditions as Example Three.

The following Table 2 gathers the results obtained in butene conversions and $C_{5+}$ selectivity, measured as described in Example Three.

EXAMPLE FIVE

This example aims to compare the performance of catalyst C of the invention with that of catalyst A of the previous method, with regards to the reaction temperature.

The alkylation is performed in the same conditions than in examples three and four. Of course the temperature and pressure must be sufficient to maintain the mix of reagents in a liquid state inside the reactor.

However, the reactor is filled with liquid isobutene prior to the reaction.

Table 3 below gathers the results obtained for the butene conversion and the $C_{5+}$ selectivity as described in Example Three.

TABLE 3

Duration 2 h 45 m

| T° (C.) | Catalyst A Conversion % | Selectivity $C_{5+}$% | Catalyst C (0.05% Na weight) Conversion % | Selectivity $C_{5+}$% |
|---|---|---|---|---|
| −30 | — | — | 30.1 | 192 |
| −26 | 35.4 | 183 | — | — |
| −20 | — | — | 50.4 | 196 |
| −10 | 44.4 | 184 | 60.2 | 187 |
| 0 | 53.0 | 175 | 70.6 | 179 |

TABLE 2

| | Catalyst A | | 0.05% LI Weight | | 0.15% LI Weight | | 0.25% LI Weight | | 0.50% LI Weight | |
|---|---|---|---|---|---|---|---|---|---|---|
| | | | | CATALYST B | | | | | | |
| Temps | Conversion (%) | Selectivity (%) | Conversion (%) | Selectivity (%) | Conversion (%) | Selectivity (%) | Conversion (%) | Selectivity (%) | Conversion (%) | Selectivity (%) |
| 5 mn | 93.4 | 238 | 96.0 | 231 | 97.2 | 232 | 99.1 | 212 | 89.4 | 212 |
| 2.17 h | 13.7 | 125 | 50.1 | 210 | 63.0 | 223 | 69.2 | 216 | 45.7 | 226 |
| 3.15 h | — | — | — | — | — | — | 29.6 | 175 | — | — |

These results show that catalyst B of the invention presents a stability clearly superior to that of catalyst A, of the previous method.

TABLE 3-continued

<u>Duration 2 h 45 m</u>

| | Catalyst A | | Catalyst C (0.05% Na weight) | |
|---|---|---|---|---|
| T° (C.) | Conversion % | Selectivity $C_{5+}$,% | Conversion % | Selectivity $C_{5+}$,% |
| 24 | 6.9 | 152 | 84.6 | 164 |
| 51 | — | — | 77.6 | 156 |

These results show that catalyst C from the invention permits a better conversion and a better selectivity in $C_{5+}$ no matter what the reactor temperature may be, and especially allows operation at temperature near ambient temperature.

What is claimed is:

1. Process for alkylation of isobutene by light olefins, comprising
subjecting a charge comprising isobutene and olefins to a reaction with an alkylation catalyst at a temperature between −20° and 100° C.,
wherein said alkylation catalyst comprises a porous support comprising alumina, on the surface of which is present at least one halogen atom, said catalyst further comprising between 0.005 and 1% by weight of at least one metal selected from Group IA and Group IIA of the Periodic Table of Elements.

2. Process according to claim 1, wherein the hourly spatial speed, expressed in weight of olefins passing on the catalyst by weight unit of the catalyst and by hour, is between 0.001 and 10 $h^{-1}$.

3. Process according to claim 2, wherein said hourly spatial speed is between 0.05 and 3 $h^{-1}$.

4. Process according to claim 1, wherein the molar ratio of isobutene to olefins is between 1 and 100.

5. Process according to claim 1, wherein the light olefins are butenes.

6. Process according to claim 1, wherein said temperature is between −5° and 35° C.

7. Process according to claim 1, wherein the halogen is chloride.

8. Process according to claim 7, wherein the catalyst contains between 2 and 10% by weight of chloride.

9. Process according to claim 8, wherein the catalyst contains between 3 and 8% by weight of chloride.

10. Process according to claim 1, wherein the catalyst contains between 0.05 and 0.5% by weight of said at least one metal selected from Group IA and Group IIA of the Periodic Table of Elements.

11. Process according to claim 1, wherein said at least one metal is selected from the group consisting of lithium, sodium, potassium, cesium, magnesium, and barium.

12. Process according to claim 1, wherein said catalyst is prepared by the following successive steps:
pre-impregnating a porous alumina support with at least one salt of a metal selected from Group IA and Group IIA of the Periodic Table of Elements, dry or in a water-based solution,
drying of the impregnated support,
calcining the support, and
chlorinating the support.

* * * * *